United States Patent [19]

Coppersmith et al.

[11] Patent Number: 4,496,657

[45] Date of Patent: Jan. 29, 1985

[54] MICROPLATE WASHER

[75] Inventors: Ward J. Coppersmith, San Diego; George B. LaMotte, III, Larkspur, both of Calif.

[73] Assignee: Scripps Clinic and Research Foundation, Calif.

[21] Appl. No.: 434,308

[22] Filed: Oct. 14, 1982

[51] Int. Cl.[3] .......................... C12M 1/00; C12M 1/32; B01L 3/00

[52] U.S. Cl. .......................... 435/287; 435/293; 422/99

[58] Field of Search .................. 435/30, 287, 291, 292, 435/293; 422/63, 99, 100; 134/21, 22.18, 102, 172, 174, 198; 141/89, 91, 92; 73/863.32

[56] References Cited

U.S. PATENT DOCUMENTS

| | | | |
|---|---|---|---|
| 3,261,208 | 7/1966 | Fisher | 73/863.32 |
| 3,536,449 | 10/1970 | Astle | 73/863.32 X |
| 3,568,735 | 3/1971 | Lancaster | 422/100 X |
| 3,609,040 | 9/1971 | Kuzel et al. | 435/30 X |
| 3,650,306 | 3/1972 | Lancaster | 422/100 X |
| 3,881,872 | 5/1975 | Naono | 134/21 X |
| 3,949,771 | 4/1976 | Dodge et al. | 134/174 X |
| 4,098,305 | 7/1978 | Gates | 141/92 |
| 4,227,886 | 10/1980 | Bullock et al. | 134/18 X |
| 4,236,825 | 12/1980 | Gilford et al. | 356/414 |
| 4,245,042 | 1/1981 | Weinstein et al. | 435/30 |
| 4,265,855 | 5/1981 | Mandle et al. | 422/63 X |

OTHER PUBLICATIONS

"Dynawasher II 96 Channel Washer/Aspirator Operating Instructions" from Dynatech Laboratories, Inc., Arlington, VA.

*Primary Examiner*—David M. Naff
*Assistant Examiner*—Randall E. Deck
*Attorney, Agent, or Firm*—Townsend and Townsend

[57] ABSTRACT

A novel apparatus is disclosed for the alternate filling and evacuation of all wells simultaneously of a multiwell microplate. The apparatus consists of a flat, horizontally disposed vacuum chamber having an upper plate and a lower plate, with a rectangular array of tubes passing through the latter such that two tubes are aligned with each well of a microplate, one for filling and the other for evacuation. The microplate is supported below the vacuum chamber with the tubes in proper alignment, and means are provided for bringing the microplate and the tubes in close proximity, for applying a vacuum to the vacuum chamber for evacuating the wells, and for supplying pressurized wash fluid to the filling tubes. The apparatus provides a faster washing process for microplates, and is more reliable and efficient than devices already known for the same or similar purposes.

10 Claims, 2 Drawing Figures

MICROPLATE WASHER

BACKGROUND OF THE INVENTION

I. Field of the Invention

A critical processing step in many genetic engineering and molecular biology techniques is the selection of a particular cell or cell colony from a multitude of similar species. Hybridoma technology, where the fusion and plating of hybrid cells generally results in several thousand clones is one example of a process requiring such selection. The clones are typically screened by immunoassay techniques to select the single clone producing the specific antibody of interest. To preserve the activity of the cells, the screening must take place within a few days. Screening is generally accomplished by the use of a series of microplates, each containing a large number of wells, each well designed to accommodate a single clone.

Screening techniques involving microplates generally involve two or more steps in each of which a reagent or reagent mixture is added to each well. For reliability and accuracy of results, the wells must be emptied between these steps, and rinsed with a washing solution to eliminate non-specifically bound reagents. It is often necessary to rinse and evacuate each of the wells in a large number of microplates several times within the course of a single screening procedure.

The present invention relates to an apparatus for the washing of all wells in a microplate at once, in a highly efficient and reliable manner.

II. Description of the Prior Art

A variety of microplate washers are commercially available. A manual device known as the "Miniwash Washer-Aspirator" is available from Dynatech Laboratories, Inc., Arlington, Va. This device is hand-operated, and capable of filling and evacuating only one row (eight wells) of a microplate at one time. A thorough wash of an entire microplate takes several minutes, and the likelihood of spillage from one well to an adjacent well is a serious disadvantage. A further manually-operated device is the "Dynawasher II", also available from Dynatech Laboratories, Inc. Although this device is designed to handle all wells in a microplate simultaneously, it has two positions, located at the extreme ends of a horizontal track, one for aspiration and the other for filling the wells with wash fluid. Finally, an automatic device bearing the name "Titertek ® Multi-Wash" is available from Flow Laboratories, Inc., McLean, Va. This device is capable of washing and filling only two rows of a microplate at a time. The mechanism is completely enclosed, precluding detection by the operator of such problems as incomplete filling or aspiration of the wells, both of which are known to plague this instrument.

SUMMARY OF THE INVENTION

An apparatus is provided for the alternate filling and evacuation of all wells simultaneously of a multi-well microplate. By virtue of its low cost, simple construction, versatility, and efficiency of operation, the apparatus of the invention overcomes the disadvantages of the prior art and offers a reliable and effective means for washing a large number of microplates in a relatively short period of time. The speed and efficiency of screening processes in multiple assay procedures is thus considerably enhanced.

The apparatus consists in general of a flat, horizontally disposed vacuum chamber having an upper plate and a lower plate, with a rectangular array of tubes passing through the latter, and arranged such that two tubes are aligned with each well of a microplate. One of the tubes of each pair serves as a filling tube and the other an evacuation tube, the latter terminating within the vacuum chamber and the former extending through the vacuum chamber and the upper plate. The vacuum chamber is positioned above a support surface parallel to the two plates containing guide means to secure the microplate in position such that each well is in alignment with a single pair of tubes. Means are provided for narrowing and widening the gap between the vacuum chamber and the microplate, as well as means for applying a vacuum to the vacuum chamber and for supplying pressurized wash fluid to the filling tubes.

A further understanding of the invention will be facilitated for reference to the attached drawings.

DETAILED DESCRIPTION OF THE DRAWINGS

Figure 1:
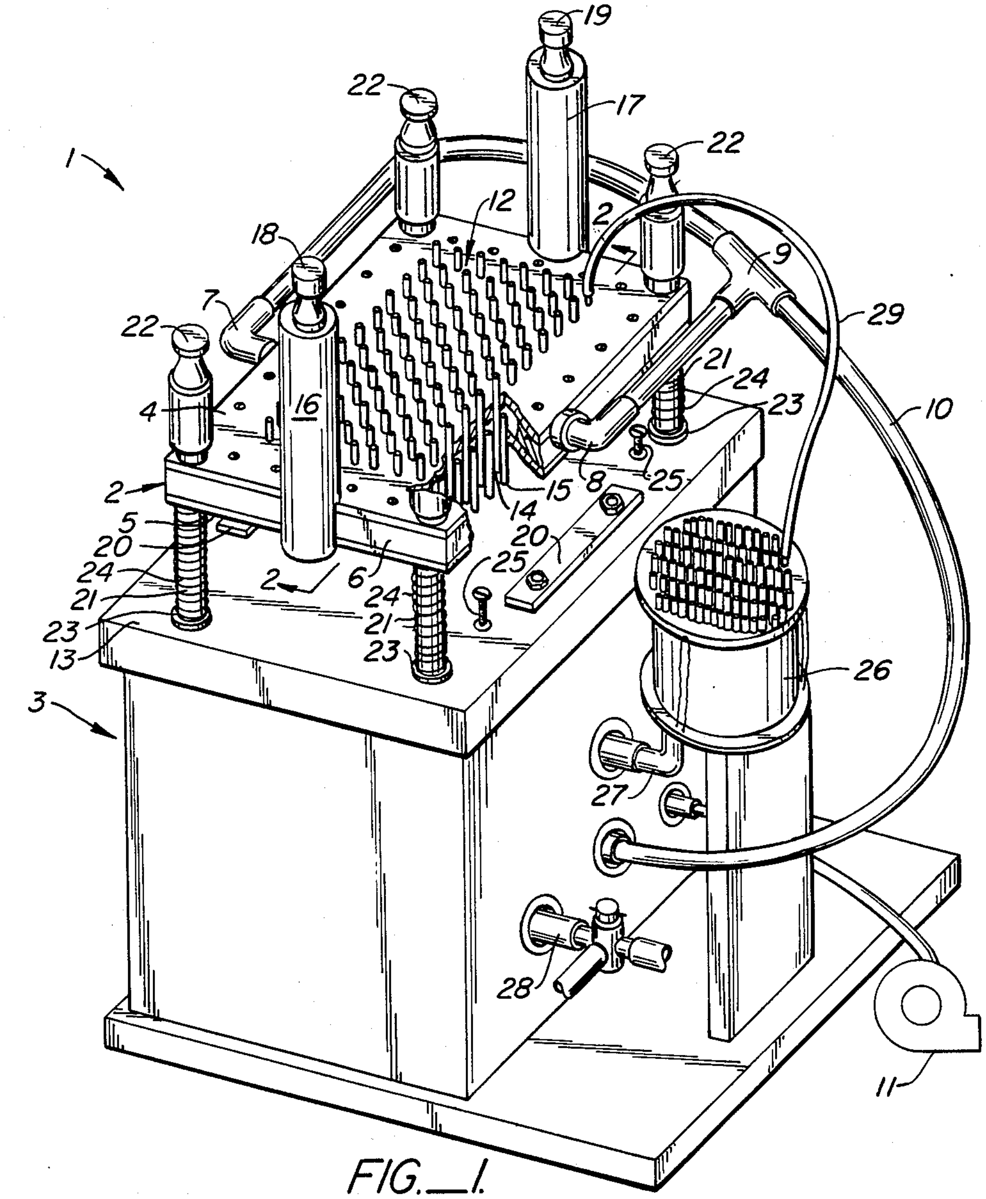
FIG. 1 is a perspective view of one embodiment of the apparatus of the present invention.

FIG. 1 illustrates a filling/evacuating apparatus 1 constituting one embodiment of the present invention. The apparatus consists of a flat horizontal vacuum chamber 2 mounted above a support 3 to permit a vertical translational movement of one with respect to the other, and with sufficient space in between to accommodate and permit the easy removal of a microplate.

The vacuum chamber is defined by a pair of parallel plates 4 and 5 spaced apart by a peripheral side wall 6 which completely encloses the chamber in air-tight fashion. Tubing connections 7 and 8 extending through the side wall into the interior of the chamber are used as means for applying a vacuum to the chamber. The connections shown in the drawing are placed at opposite sides of the chamber for an evenly-distributed evacuation, and are connected through a T-shaped connection 9 to a common conduit 10. Connection of line 10 to a vacuum source 11 is obtained through a valve or switching mechanism (not shown), which can be conveniently located in the interior of the microplate's support base 3 with an accessible control. Any conventional vacuum source, such as pumps, aspirators, etc., can be used. The degree of vacuum is not critical, provided that it is sufficient to effect evacuation from all wells of the microplate within a reasonable period of time. In most applications, a vacuum of at least about ten inches (25.4 cm) of mercury will be most convenient, preferably at least about twenty inches (50.8 cm).

Passing through the lower plate 5 of the vacuum chamber are a series of tubes 12 arranged in a rectangular array. The tubes are spaced such that two such tubes are aligned with each well of a microplate when the latter is resting on the upper surface 13 of the support 3. The tubes are of sufficient number to include one pair for each microplate well. Since most microplates contain 96 wells, arranged in twelve rows of eight each, the preferred number of tubes is 192. Typical 96-well microplates have a well spacing of approximately 9 mm, center-to-center. Each pair of tubes, therefore, is spaced approximately 9 mm from the next. The two tubes of each pair are sufficiently close to each other to both come within each well perimeter, yet far enough apart to prevent a direct flow path from one to the other.

Each of the tubes 12 extends a short distance below the lower plate 5. The two tubes in each pair, designated hereinafter as a filling tube 14 and an evacuation tube 15, respectively, extend for unequal distances below the bottom plate, the filling tube being the less extended, and the evacuation tube the more extended. The length of each tube is sufficient to extend into the microplate wells when the vacuum chamber 2 is lowered to its lowermost position. A convenient length is on the order of one inch (2.54 cm) or less, preferably about one-half inch (1.27 cm). The difference in length between the two tubes is preferably less than the depth of each well. The purpose of the difference in length is to optimize the filling and evacuation functions of the tubes—i.e., when the apparatus is in operation, the evacuation tubes will be lowered so that their lower ends are sufficiently close to the bottom of the well to permit evacuation of substantially all the liquid from the well, whereas the filling tube will terminate at a sufficient height above the bottom of the well to permit filling of the well with a minimum of splashing and flow obstruction. For most wells, a length difference ranging from about 0.05 inch (0.127 cm) to about 0.4 inch (1.02 cm) is appropriate.

The evacuation tubes 15 terminate at their upper end inside the vacuum chamber 2 in order that the liquid drawn up from the wells when a vacuum is applied will enter the chamber and pass out of the chamber through the side vacuum tubing connections 7 and 8. Preferably, the evacuation tubes extend a short distance above the lower plate 5 to prevent spillage back through the tubes when the vacuum is turned off. The filling tubes 14 extend upward through the interior of the vacuum chamber and through the upper plate 4, such that there is no possibility of leakage between the interior of the filling tubes and the vacuum chamber. Pressurized wash fluid is applied to each of these tubes, which in turn distribute the fluid to each of the wells in the microplate.

In the embodiment shown in FIG. 1, each of the filling tubes is fed by a length of flexible tubing (only one such length is shown in the drawing) connecting the tube to a reservoir or chamber which retains the liquid under pressure and permits the separation of air bubbles.

The support 3 is comprised of any structure capable of forming a flat horizontal surface 13 to hold a microplate. In the embodiment shown in FIG. 1, the support is an enclosed structure, which houses the valves or switching means governing the flow of pressurized wash fluid to the filling tubes and the access to the vacuum source. Solenoid valves are particularly useful as switching means for both functions, and an enclosed structure such as that shown, which houses the solenoids, is particularly efficient, and thus preferred. Control switches for the solenoids can be located at any convenient location provided they are accessible to the operator. In the drawing, the switches are mounted atop posts 16 and 17 extending upward from the vacuum chamber. Switch 18 controls the valve on the pressurized fluid line and is activated for the wash step, and switch 19 controls the valve on the vacuum line and is activated for the evacuation step.

Attached to the microplate support surface 13 are guide means 20 for fixing the position of a microplate. Since microplates are generally of rectangular configuration, the guide means will typically consist of three protrusions with straight edges (along the inside of each), positioned to abut three sides of the microplate (only two are visible in FIG. 1), with the fourth side (shown as the forward end) left open to permit easy placement and removal of the microplate by sliding the plate along the surface 13. The protrusions are shown as flat bars in the drawing, and can be either part of the surface 13, separate pieces permanently attached to the surface (as shown), or separate pieces attached in an adjustable manner so that their spacing can be modified to accommodate microplates of different dimensions. In any case, the guide means are positioned to secure each well of the microplate beneath a corresponding pair of filling and evacuation tubes.

The position of the vacuum chamber 2 above the support surface 13 is fixed by any conventional means which will prevent motion in the horizontal direction. The embodiment shown in the drawing consists of four posts 21, one at each corner of the chamber, each with a knob 22 extending above the chamber. The posts 21 are mounted rigidly on the support 3 by attachment means 23. When posts 16 and 17 are grasped by an operator and pushed down, the entire vacuum chamber slides down the rigid posts 21 and the springs 24 on the posts 21 compress. The vacuum chamber 3 is thus movable and the support surface 13 is stationary, the posts serving to align the vacuum chamber above the support such that the upper and lower plates of the vacuum chamber and the support surface are parallel to one another, and vertical alignment of the tube pairs with the corresponding wells is maintained at all times.

In an alternative embodiment, the vacuum chamber 2 is rigidly affixed to the support 3 and the support surface 13 is vertically movable.

In either embodiment, stop means 25 are provided for setting a minimum distance between the lower plate 5 of the vacuum chamber and the microplate support surface 13. For efficient operation of the apparatus, the minimum distance is set to bring the exposed end of each evacuation tube sufficiently close to the bottom of the microplate well over which it is aligned to permit efficient evacuation of substantially all of the liquid from each well. Preferably, the stop means are adjustable so that wells of different depths can be accommodated. The stop means can be affixed to either the posts 21, the lower plate 5 of the vacuum chamber or the microplate support surface 13, although the latter is preferred for ease of access. In the embodiment shown in the drawing, the stop means are set screws. Any configuration, however, which sets a minimum distance can be used.

For enhanced efficiency of operation and uniformity in filling all wells of the microplate, it is preferable to include means for removing air bubbles from the wash liquid. In the embodiment shown in FIG. 1, the wash liquid is fed first to a bubble chamber 26 which permits the bubbles to combine with each other and separate from the bulk of the liquid. Prior to operation of the apparatus, the chamber 26 is filled with liquid through inlet line 27 controlled by an interior valve (not shown) fed by line 28. The liquid in the chamber is then allowed to remain static while the air bubbles collect at the top. Further pressurized liquid is then fed through line 27 and the air is forced out of the bubble chamber through the flexible tubing 29 and the filling tubes 14 until all filling passages are filled with liquid. An even distribution of wash liquid among all wells will then result. The bubble chamber shown in FIG. 1 also serves to distribute the wash liquid among the lines going to each well.

The materials of construction to be used in the apparatus of the invention are not critical, and can vary widely. Preferably, non-corrosive materials are used since the wash solution is frequently a saline solution. The filling and evacuation tubes may conveniently be constructed from small bore metal tubing, preferably stainless steel of the 18-8 series. The size of the tubing is likewise non-critical, but is preferably small enough to readily permit the filling of the wells by discrete drops when pressure is applied to the bubble chamber. Tubing of a size on the order of approximately 14 gauge is the most convenient.

It is further preferred that transparent materials be used for the vacuum chamber, bubble chamber, and whatever transfer lines are used. This will permit plugs to be more easily discerned, and facilitate the avoidance of air bubbles. Plastics and similar materials are useful in this regard.

Figure 2:
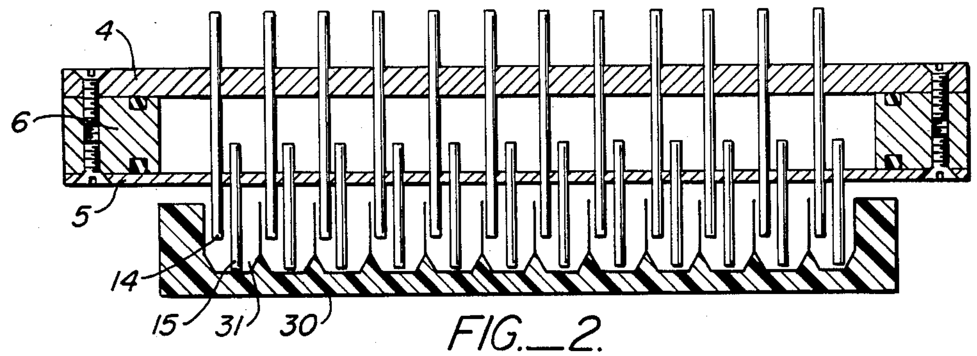
FIG. 2 is a sectional view of the vacuum chamber and one row of filling and evacuation tubes, taken along Line 2—2 of FIG. 1.

In FIG. 2, a typical cross-sectional arrangement of the vacuum chamber 2 of FIG. 1 is shown, taken along line 2—2 of FIG. 1. The evacuation tubes 15 and the filling tubes 14 are shown with the microplate 30 in position. One filling tube and one evacuation tube are aligned with each well 31 of the microplate. The lower end of the evacuation tube is positioned very close to the bottom of the well so that substantially complete evacuation is achieved.

At the option of the manufacturer, further features can be incorporated into the design to insure complete washing and evacuation without back spillage of wash fluid. As one example, a switch controlling the vacuum solenoid can be installed for activation by the upward movement of the vacuum chamber 2 (or the lowering of the support surface 13 for embodiments where the vacuum chamber is immovable). This will prevent backward spillage from the vacuum chamber into the wells in the event of jostling of the apparatus when the vacuum chamber is lifted. A magnetic reed switch or Hall effect switch is suitable for this purpose.

Finally, although operation of the filling and evacuation functions of the apparatus can be manually controlled as shown, a further variation would be the use of a microprocessor or similar device to program the functions for automated operation.

The foregoing description is offered solely for purposes of illustration; the invention is not intended to be limited to the particular features of construction and operation shown or described. Numerous modifications and variations of the above still falling within the spirit and scope of the invention as claimed hereinbelow will be readily apparent to those skilled in the art.

What is claimed is:

1. An apparatus for the alternate filling and evacuation of all wells simultaneously of a multiwell microplate, said apparatus comprising:

a vacuum chamber defined by two parallel plates designated an upper plate and a lower plate, respectively, said plates separated by peripheral spacing means, said lower plate having affixed therein a plurality of tubes spaced apart from each other, each said tube passing through said lower plate and perpendicular thereto, said tubes forming a rectangular array such that, when said chamber is superimposed over said microplate, a pair of said tubes is aligned with each well of said microplate, the portions of each tube of said pair which extend below said lower plate being of unequal length, the tube with the shorter portion below the lower plate being designated a filling tube and the tube with the longer portion below the lower plate being designated an evacuation tube, said filling tube extending upward through said chamber and said upper plate, and said evacuation tube terminating within said chamber above the lower plate, a support for said microplate, said support comprising a substantially flat horizontal surface containing guide means adapted to secure said microplate in a predetermined position on said support surface, means for maintaining said vacuum chamber in vertical alignment with said support with said upper and lower plates of said vacuum chamber and said support surface in parallel relation, and for narrowing and widening the distance between said vacuum chamber and said support surface while substantially maintaining said parallel relation, stop means for setting a minimum spacing distance between said vacuum chamber and said support surface such that when said distance is at said minimum, the exposed end of each said evacuation tube is sufficiently close to the bottom of the corresponding well in said microplate to permit evacuation of substantially all liquid from said well, means for applying a vacuum to said vacuum chamber, and means for supplying pressurized fluid to each said filling tube at the upper end thereof.

2. An apparatus according to claim 1 in which the difference in length between said portions of said filling and evacuation tubes which extend below said lower plate is less than the depth of said well.

3. An apparatus according to claim 1 in which said guide means on said support surface are adjustable to accommodate microplates of different lateral dimensions.

4. An apparatus according to claim 1 in which said stop means are affixed to said support surface and are adjustable to accommodate microplates of different thicknesses.

5. An apparatus according to claim 1 in which said support surface is fixed and said vacuum chamber is movable in the vertical direction, and said narrowing and widening of said distance between said vacuum chamber and said support surface is achieved by lowering and raising said vacuum chamber, respectively.

6. An apparatus according to claim 1 in which said vacuum chamber is fixed and said support surface is movable in the vertical direction, and said narrowing and widening of said distance between said vacuum chamber and said support surface is achieved by raising and lowering said support surface, respectively.

7. An apparatus according to claim 1 in which said upper and lower plates and said peripheral spacing means of said vacuum chamber are transparent.

8. An apparatus according to claim 1 in which the number of tubes amounts to one said pair for each well of a 96-well microplate.

9. An apparatus according to claim 1 further comprising means for removing air or vapor bubbles from said pressurized fluid.

10. An apparatus according to claim 1 further comprising switching means for individually engaging each of said vacuum means and said pressurized fluid supplying means with said vacuum chamber and said filling tubes, respectively.

* * * * *